(12) United States Patent
Park

(10) Patent No.: US 11,608,070 B2
(45) Date of Patent: Mar. 21, 2023

(54) SYSTEM AND METHOD FOR MONITORING DRIVER

(71) Applicant: HYUNDAI MOBIS CO., LTD., Seoul (KR)

(72) Inventor: Ge O Park, Seoul (KR)

(73) Assignee: HYUNDAI MOBIS CO., LTD., Seoul (KR)

( * ) Notice: Subject to any disclaimer, the term of this patent is extended or adjusted under 35 U.S.C. 154(b) by 0 days.

(21) Appl. No.: 17/385,154

(22) Filed: Jul. 26, 2021

(65) Prior Publication Data

US 2022/0032923 A1    Feb. 3, 2022

(30) Foreign Application Priority Data

Jul. 29, 2020 (KR) .................. 10-2020-0094559

(51) Int. Cl.
| | |
|---|---|
| *G06N 3/02* | (2006.01) |
| *B60W 40/09* | (2012.01) |
| *B60W 60/00* | (2020.01) |
| *G06V 20/56* | (2022.01) |
| *A61B 5/024* | (2006.01) |
| *A61B 5/18* | (2006.01) |
| *B60W 40/08* | (2012.01) |

(52) U.S. Cl.
CPC ......... *B60W 40/09* (2013.01); *A61B 5/02438* (2013.01); *A61B 5/18* (2013.01); *B60W 60/0018* (2020.02); *G06N 3/02* (2013.01); *G06V 20/588* (2022.01); *B60W 2040/0872* (2013.01); *B60W 2520/14* (2013.01); *B60W 2540/18* (2013.01); *B60W 2540/221* (2020.02); *B60W 2556/05* (2020.02)

(58) Field of Classification Search
CPC ............ B60W 40/08; B60W 60/0018; B60W 2540/221; G06V 20/588
See application file for complete search history.

(56) References Cited

U.S. PATENT DOCUMENTS

| | | | |
|---|---|---|---|
| 5,769,085 A * | 6/1998 | Kawakami | A61B 5/024 |
| | | | 600/519 |
| 7,580,820 B2 * | 8/2009 | Sawada | B60W 50/10 |
| | | | 701/65 |

(Continued)

FOREIGN PATENT DOCUMENTS

| | | |
|---|---|---|
| EP | 3 489 066 A2 | 5/2019 |
| KR | 10-2016-0129984 A | 11/2016 |
| KR | 10-2016-0133284 A | 11/2016 |

OTHER PUBLICATIONS

Extended European Search Report issued in corresponding European Patent Application No. 21186455.8 dated Jan. 4, 2022.

*Primary Examiner* — Qutbuddin Ghulamali

(74) *Attorney, Agent, or Firm* — Morgan, Lewis & Bockius LLP

(57) ABSTRACT

A system for monitoring a driver comprises that a first sensor configured to detect first physical condition information of the driver, a second sensor configured to detect first driving state information of a vehicle; and a controller configured to determine whether a physical condition of the driver is abnormal on the basis of the first physical condition information, and determine whether a driving pattern of the driver is abnormal on the basis of the first driving state information.

20 Claims, 3 Drawing Sheets

(56) References Cited

U.S. PATENT DOCUMENTS

| | | | | |
|---|---|---|---|---|
| 8,311,702 | B2* | 11/2012 | Miki | G06V 40/1382 |
| | | | | 382/115 |
| 10,503,987 | B2* | 12/2019 | Banno | A61B 5/18 |
| 2016/0311440 | A1* | 10/2016 | Gan | B60K 28/06 |
| 2018/0091085 | A1* | 3/2018 | Tamagaki | B60W 30/06 |
| 2019/0056732 | A1 | 2/2019 | Aoi et al. | |
| 2019/0135291 | A1* | 5/2019 | Sim | B60W 30/10 |

* cited by examiner

SYSTEM AND METHOD FOR MONITORING DRIVER

CROSS-REFERENCE TO RELATED APPLICATION

This application claims priority to Korean Patent Application No. 10-2020-0094559, filed on Jul. 29, 2020, in the Korean Intellectual Property Office, the disclosure of which is incorporated herein by reference.

TECHNICAL FIELD

The present disclosure relates to a system and method for monitoring a driver, and more specifically, to a system and method for monitoring a driver which can determine an abnormal condition of a driver in consideration of a physical condition of the driver or a driving state of a vehicle, warn the driver of the abnormal condition, and safely move the vehicle to a safe zone.

BACKGROUND

As falling asleep at the wheel has become a social issue as a major cause of traffic accidents, vehicle manufacturers have developed and applied drowsy driving prevention systems for recognizing the face of a driver to determine whether the driver feels sleepy in advance and warning the driver in advance.

However, conventional systems simply recognize the face of a driver captured using a camera and determine whether the driver is driving through image processing and thus cannot perform accurate face recognition in an environment in which the face of a driver is hardly recognized through the camera (e.g., at night, a state in which external strong light shines on a driver's seat, etc.).

In addition, conversional systems determine whether a driver is sleepy mainly on the basis of the appearance of the eyes of the driver in a recognized face and thus cannot recognize a condition in which the driver cannot drive due to an unexpected abnormal physical condition of the driver other than drowsiness.

Furthermore, conventional systems merely take measures such as sounding an alarm upon recognition of drowsiness of a driver, and thus the driver may continuously drive a vehicle even in a state in which the driver cannot drive, resulting in serious accidents.

The information included in this Background section is only for enhancement of understanding of the general background of the present disclosure and may not be taken as an acknowledgement or any form of suggestion that this information forms the prior art already known to a person skilled in the art.

SUMMARY

The present disclosure has been made in view of the above problems, and it is an object of the present disclosure to provide a system and method for monitoring a driver which can determine an abnormal condition of a driver in consideration of various conditions of the driver, vehicle states, and driving environments and move a vehicle to a safe position according to a determination result as well as determining drowsiness of the driver by recognizing the face of the driver through an image captured using a camera.

In accordance with the present disclosure, the above and other objects can be accomplished by the provision of a system for monitoring a driver, including a first sensor configured to detect first physical condition information of the driver, a second sensor configured to detect first driving state information of a vehicle, and a controller configured to determine whether a physical condition of the driver is abnormal on the basis of the first physical condition information and to determine whether a driving pattern of the driver is abnormal on the basis of the first driving state information.

In an embodiment of the present disclosure, the controller may include a storage configured to store big data analysis values regarding second physical condition information of the driver, and the controller is further configured to determine whether a physical condition of the driver is abnormal on the basis of a result of comparison between the first physical condition information and the second physical condition information.

In an embodiment of the present disclosure, the first sensor may include a wearable device configured to be worn by the driver and configured to detect a heart rate of the driver and to transmit the heart rate to the controller through wireless communication or a heart rate monitor in a steering wheel of the vehicle and configured to detect a heart rate of the driver through a hand of the driver in contact with the heart rate monitor.

In an embodiment of the present disclosure, the controller may include a storage configured to store big data analysis values regarding second driving state information, and the controller is further configured to determine whether the driving pattern is abnormal on the basis of a result of comparison between the first driving state information and the second driving state information.

In an embodiment of the present disclosure, the second sensor may include at least one of a camera configured to capture a front view image of the vehicle, a yaw sensor configured to measure a yaw value of the vehicle, or a steering angle sensor configured to detect a steering angle of the vehicle.

In an embodiment of the present disclosure, the controller may be further configured to guide the vehicle to a safe zone and to control the vehicle to stop in the safe zone upon determining that at least one of the physical condition of the driver is abnormal or the driving pattern is abnormal.

In an embodiment of the present disclosure, the system further comprises an image sensor configured to sense objects around the vehicle and capture images around the vehicle, the controller may determine an outermost lane of a road and an outermost structure of the road on the basis of images captured by the image sensor upon determining that at least one of the physical condition of the driver is abnormal or the driving pattern is abnormal, check following vehicles in a blind-spot through images captured by the image sensor, controls the vehicle to move toward an edge of the road by adjusting a steering wheel of the vehicle while reducing a vehicle speed, and controls the vehicle to stop after arrival at the edge of the road. The image sensor includes at least one of a camera capturing a front view image of the vehicle, a radar, or a Lidar.

In an embodiment of the present disclosure, the controller may further include a storage including at least one of a deep learning network configured to detect the outermost lane from the images captured by the image sensor or a deep learning network configured to detect the outermost structure of the road, and the controller may detect at least one of the outermost lane or the outermost structure by inputting the captured images or an input signal of the image sensor to the deep learning network.

In accordance with another aspect of the present disclosure, there is provided a method for monitoring a driver, by a controller, including receiving first physical condition information of the driver detected by a first sensor of a vehicle and first driving state information of the vehicle detected by a second sensor of the vehicle, determining whether a physical condition of the driver is abnormal on the basis of the first physical condition, and determining whether a driving pattern of the driver is abnormal on the basis of the first driving state information. Upon determining at least one of the physical condition or the driving pattern is abnormal, the method automatically controls the vehicle to move to a safe zone.

In an embodiment of the present disclosure, the determining whether the physical condition of the driver is abnormal may include determining whether the physical condition of the driver is abnormal on the basis of a result of comparison between big data analysis values regarding second physical condition information of the driver and the first physical condition information.

In an embodiment of the present disclosure, the first sensor may include a wearable device configured to be worn by the driver and configured to detect a heart rate of the driver and to transmit the heart rate to the controller through wireless communication or a heart rate monitor included in a steering wheel of the vehicle and configured to detect a heart rate of the driver through a hand of the driver in contact with the heart rate monitor.

In an embodiment of the present disclosure, the determining may include determining whether the driving pattern is abnormal on the basis of a result of comparison between big data analysis values regarding second driving state information and the first driving pattern information.

In an embodiment of the present disclosure, the second sensor may include at least one of a camera configured to capture a front view image of the vehicle, a yaw sensor configured to measure a yaw value of the vehicle, or a steering angle sensor configured to detect a steering angle of the vehicle.

In an embodiment of the present disclosure, the method may further include performing, by the controller, autonomous driving control to guide the vehicle to the safe zone and to control the vehicle to stop in the safe zone upon determining that at least one of the physical condition of the driver is abnormal or the driving pattern is abnormal.

In an embodiment of the present disclosure, the performing of autonomous driving control may include, upon determining that the physical condition of the driver is abnormal or the driving pattern is abnormal, detecting an outermost lane or an outermost structure of a road on the basis of objects sensed around the vehicle or images captured around the vehicle by an image sensor, and checking following vehicles through the objects sensed in a blind stop by the image sensor, controlling the vehicle to move toward an edge of the road by adjusting a steering wheel of the vehicle while reducing a vehicle speed, and controlling the vehicle to stop after arrival at the edge of the road. The image sensor includes at least one of a camera capturing a front view image of the vehicle, a radar, or a Lidar In an embodiment of the present disclosure, the performing of the autonomous driving control may include detecting the outermost lane or the outermost structure by inputting the images to a deep learning network configured to detect the outermost lane from the images or an input signal of the image sensor to a deep learning network configured to detect the outermost structure of the road from the input signal.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION

Hereinafter, a driver monitoring system and method according to various embodiments will be described in detail with reference to the attached drawings.

Figure 1:
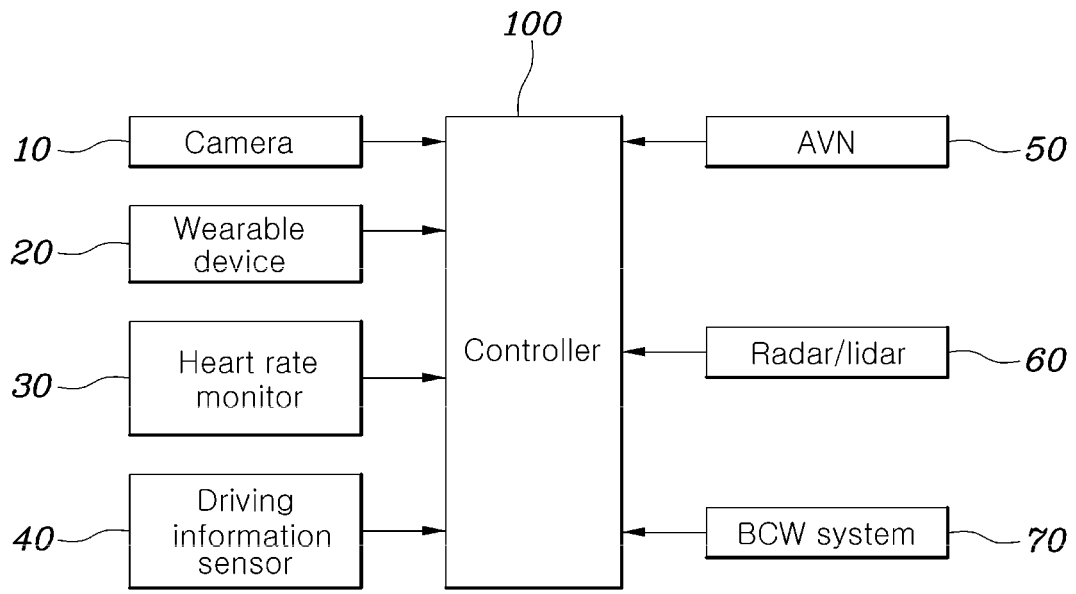
FIG. 1 is a block diagram illustrating a system for monitoring a driver according to an embodiment of the present disclosure.
Figure 2:
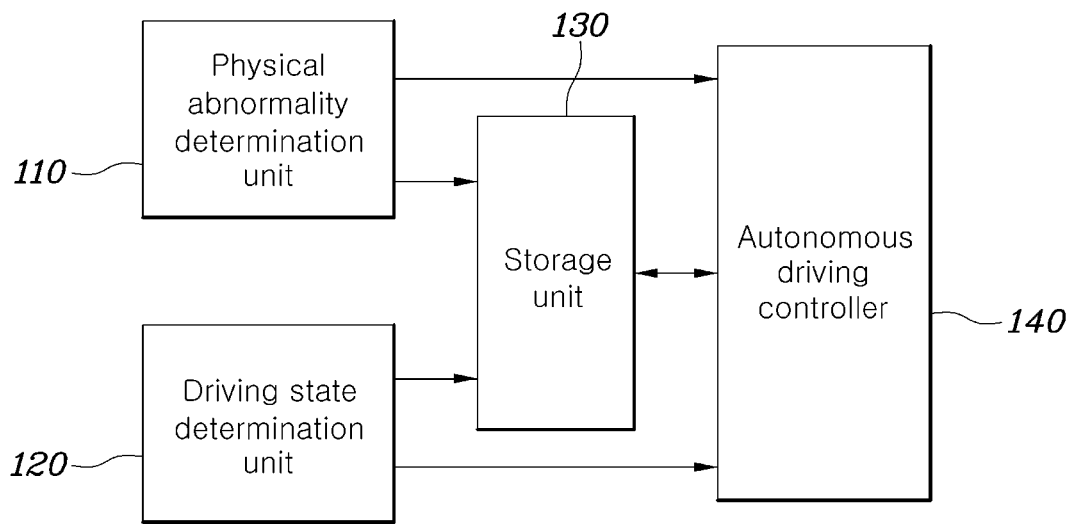
FIG. 2 is a block diagram illustrating a driver monitoring controller according to an embodiment of the present disclosure in more detail.

FIG. 1 is a block diagram illustrating a system for monitoring a driver according to an embodiment of the present disclosure. FIG. 2 is a block diagram illustrating a driver monitoring controller according to an embodiment of the present disclosure in more detail.

Referring to FIG. 1, the system for monitoring a driver according to an embodiment of the present disclosure may include various sensors 10, 20, 30, and 40 that detect physical condition information of a driver and driving state information of a vehicle, and a controller 100 that determines a condition of the driver on the basis of signals input from the sensors 10, 20, 30, and 40 and warns the driver of his/her abnormal condition or moves the vehicle to a safe zone through autonomous driving and then stop the vehicle upon determining that the condition of the driver is abnormal.

The sensors may be divided into a first sensor for detecting physical condition information of a driver and a second sensor for detecting driving state information of a vehicle.

For example, the first sensor may include a wearable device 20 such as a smart watch capable of measuring the heart rate of a driver, a heart rate monitor 30 that is provided in a steering wheel of a vehicle and can measure the heart rate of a driver through the hands of the driver in contact therewith when the driver holds the steering wheel with the hands, etc.

In addition, the second sensor is a sensor for detecting a vehicle driving pattern and may include a camera that captures a front view image of a vehicle and a driving information sensor 40 such as a yaw sensor that measures a yaw value of the vehicle or a steering angle sensor that detects a steering angle of the vehicle as a sensor capable of detecting a behavior of the vehicle in a state in which the driver is drowsy or cannot drive the vehicle.

The controller 100 may include a physical abnormality determination unit 110 capable of determining an abnormal physical condition of the driver using information collected from the first sensor and a driving state determination unit

120 capable of determining whether a driving pattern is abnormal using information collected from the second sensor.

In addition, the controller may further include a storage 130 storing reference values used for the physical abnormality determination unit 110 and the driving state determination unit 120 to determine an abnormality.

The storage 130 may store big data analysis values regarding physical condition information of the driver or big data analysis values regarding a driving pattern of the driver.

For example, the storage 130 may store a normal heart rate range of the driver which is derived using previously accumulated big data information about heart rates of the driver or a normal heart rate range derived using big data information collected from random people corresponding to the age and the sex of the driver. The physical abnormality determination unit 110 may determine whether a physical condition of the driver is abnormal by comparing information on the normal heart rate range which is big data analysis information stored in the storage 130 with real-time heart rate information of the driver received through the first sensor.

In addition, the storage 130 may store big data information obtained by analyzing previously accumulated driving pattern related information of the driver. Here, the big data information may include positions of lanes which can be detected through images collected using a camera, change in a yaw value of the vehicle detected through a yaw sensor, change in a steering angle indicating a degree of rotation of the steering wheel, etc. The driving state determination unit 120 may compare patterns of lane positions in front view images, yaw value change, steering angle change, etc. which are big data analysis information stored in the storage 130 with a real-time detection value change pattern received through the second sensor, and when a difference between the patterns is a predetermined level or more, determine that a driving pattern difference is caused by an abnormal condition of the driver.

Although the camera 10, the yaw sensor, and the steering angle sensor are exemplified as the second sensor in the above description, various other sensors by which a driving pattern of the driver, that is, a driving habit of the driver, can be determined may be selectively employed.

When the physical abnormality determination unit 110 and the driving state determination unit 120 of the controller 100 determine that an abnormality has occurred, the controller 100 may transmit a warning signal to an audio video navigation (AVN) system 50 of the vehicle, and the AVN system 50 may warn the driver through visual and auditory methods upon reception of the warning signal.

In addition, the controller 100 may further include an autonomous driving controller 140 that controls the vehicle to automatically move to a safe zone when the driver does not drive the vehicle to the safe zone or maintains an abnormal physical condition or driving pattern after the warning signal is output.

The autonomous driving controller 140 may control the vehicle to move to the edge of a road on which the vehicle is traveling and then stop using the camera 10, a radar/lidar 60, and a blind-spot collision warning (BCW) system 70 provided in the vehicle.

Figure 3:
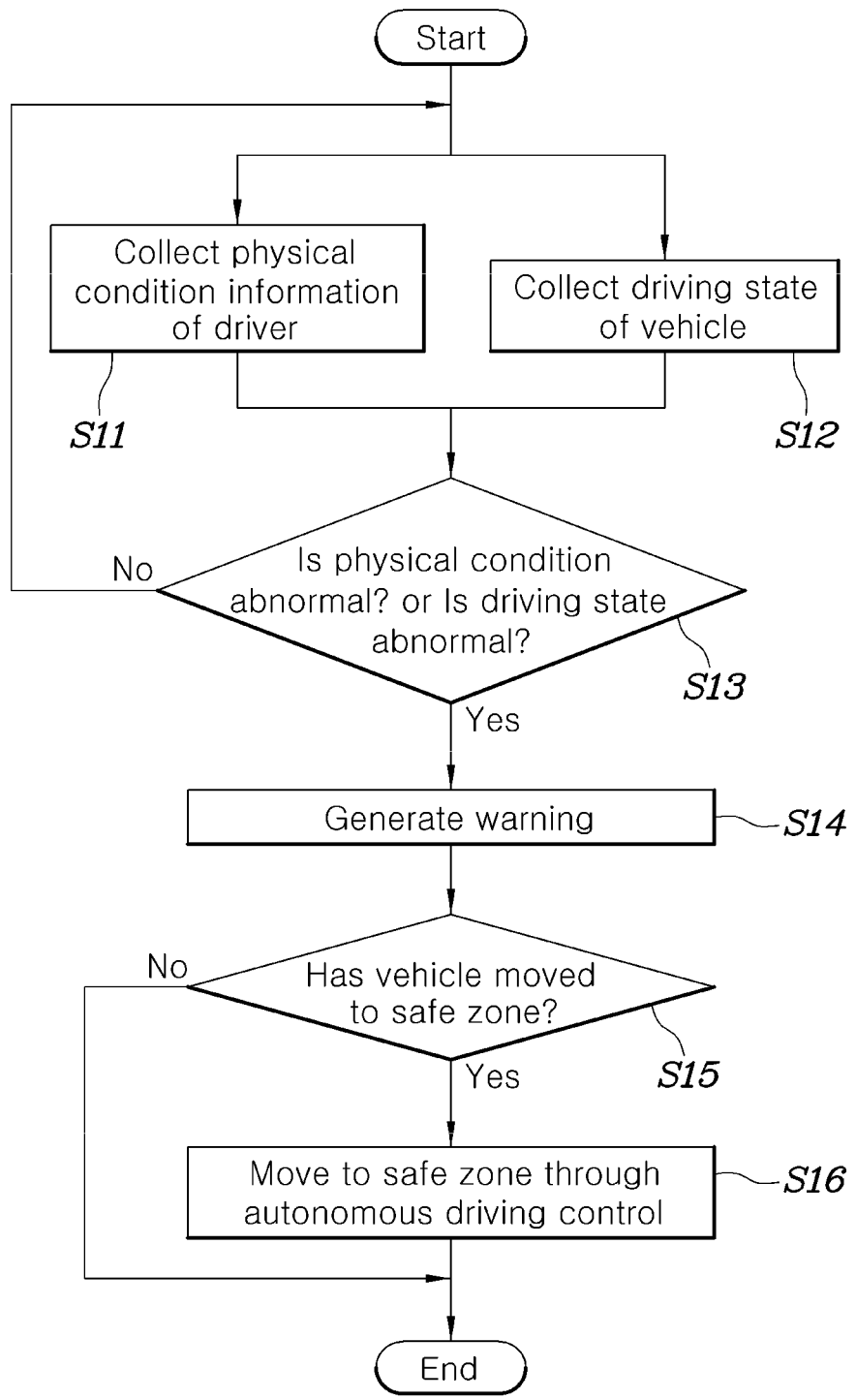
FIG. 3 is a flowchart illustrating a method for monitoring a driver according to an embodiment of the present disclosure.

FIG. 3 is a flowchart illustrating a method for monitoring a driver according to an embodiment of the present disclosure.

As illustrated in FIG. 3, the method for monitoring a driver according to an embodiment of the present disclosure is implemented by the above-described system for monitoring a driver and may include a step S11 and S12 of receiving physical condition information of a driver and driving state information of a vehicle from the sensors 10, 20, 30, and 40 included in the vehicle, and a step S13 of determining, by the controller 100, an abnormality on the basis of the received physical condition information and the driving state information of the vehicle.

The physical condition information of the driver may be measured by a heart rate measurement sensor included in a wearable device (smart watch) 20 worn by the driver or the heart rate monitor 30 included in the steering wheel of the vehicle and may be provided to the controller 100 through a known wireless communication method or an in-vehicle signal communication method (e.g., CAN).

Further, driving state information of the vehicle may be an image captured by the camera 10 or information obtained by analyzing the image, or information detected through the driving information sensor 40, such as a yaw sensor or a steering angle sensor, and may be provided to the controller 100 through a known wireless communication method or an in-vehicle signal communication method.

Subsequently, the physical abnormality determination unit 110 of the controller 100 may determine whether the physical condition of the driver is abnormal by comparing information on a normal heart rate range that is big data analysis information stored in the storage 130 with received real-time heart rate information of the driver in step S13. Likewise, the driving state determination unit 120 of the controller 100 may compare patterns of lane positions in front view images, yaw value change, steering angle change, etc. which are big data analysis information stored in the storage 130 with a real-time detection value change pattern received through the second sensor, and when a difference between the patterns is a predetermined level or more, determine that a driving pattern difference is caused by an abnormal condition of the driver in step S13.

Upon determining that the physical condition of the driver is abnormal or a difference between a driving pattern of the vehicle and a previous driving pattern is a predetermined level or more in step S13, the controller 100 may transmit a warning signal to the AVN system 50 of the vehicle to cause the AVN system 50 to warn the driver through visual and auditory methods (S14).

Subsequently, the controller 100 may check whether the vehicle has moved to a safe zone and stopped (S15). After a warning is generated in step S14, the controller 100 may determine that additional follow-up measures are unnecessary if the physical condition or driving pattern of the driver returns to a normal state or the driver moves the vehicle to a safe zone and stops the vehicle and may determine that the driver keeps driving in the abnormal condition despite the warning if not (S15).

If follow-up measures (moving to a safe zone or improving a physical condition/driving state) according to the warning are not taken in step S15, the autonomous driving controller 140 of the controller 100 may cause the vehicle to automatically move to a safe zone using various sensors and systems necessary for autonomous driving provided in the vehicle (S16).

Figure 4:
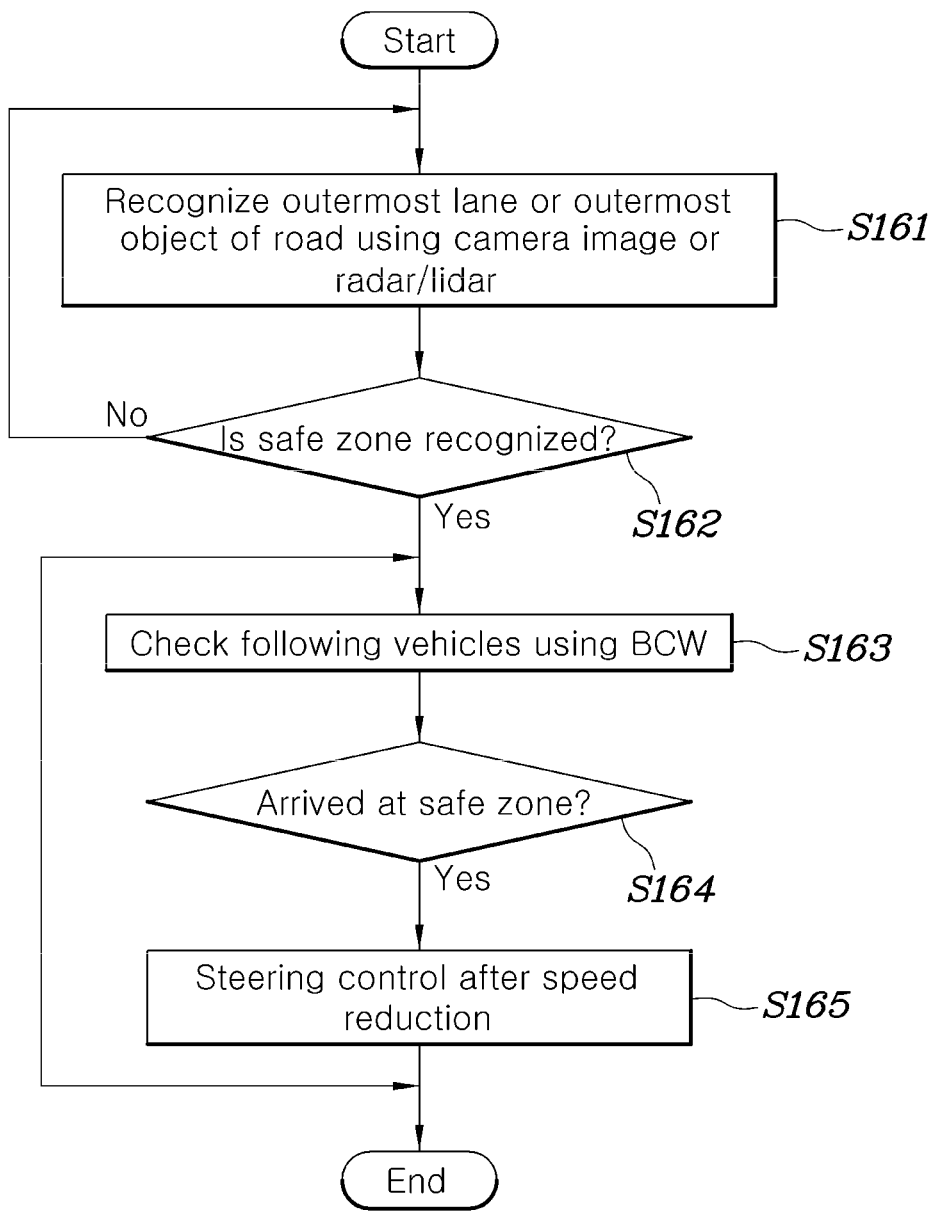
FIG. 4 is a flowchart illustrating a method of moving a vehicle to a safe zone through autonomous driving control applied to the method for monitoring a driver according to an embodiment of the present disclosure.

FIG. 4 is a flowchart illustrating a method of moving a vehicle to a safe zone through autonomous driving control applied to the method for monitoring a driver according to an embodiment of the present disclosure.

Referring to FIG. 4, upon determining that the vehicle needs to be moved to a safe zone and stopped through autonomous driving, the controller 100 may recognize an outermost lane or an outermost structure (a guardrail, a wall, or the like) of a road on which the vehicle is traveling using the camera 10 provided in the vehicle or the radar/lidar 60 capable of detecting an object in front of the vehicle (S161). The controller 100 may recognize the outermost lane or the outermost structure through an image captured using the camera in the case of driving in the daytime which allows high-quality imaging and may recognize the lane in a manner of recognizing the outermost structure through the radar/lidar 60 and then confirming the position of the recognized outermost structure in an image captured by the camera 10 in the case of driving at night. Of course, position information of the vehicle and map information derived from the AVN system 50 provided in the vehicle may be used to recognize a lane or a safe zone.

Upon confirming that there is a safe zone in which the vehicle can stop through the outermost lane or the outermost structure recognized in step S161 in step S162, the controller 100 may check whether another vehicle is approaching in a blind spot, particularly, in a lane outside the lane in which the vehicle is traveling using the BCW system 70 of the vehicle (S163).

Subsequently, the controller 100 may control the vehicle to decrease the speed and then move to the outside lane by controlling the steering wheel upon confirming that there is no vehicle approaching in the blind spot or a sufficient safety distance is secured (S164). Here, the controller 100 may control the vehicle speed such that a sufficient distance from a preceding object can be secured using the radar/lidar 60.

When the vehicle arrives at the recognized safe zone after checking the area behind the vehicle, reducing the vehicle speed and changing lanes, the controller 100 may stop the vehicle and end autonomous driving control (S165). After the vehicle arrives at the safe zone, the controller 100 may notify a control center of occurrence of the abnormal condition of the driver using a long distance communication function or a designated telephone number.

As described above, according to the system and method for monitoring a driver of various embodiments of the present disclosure, it is possible to rapidly detect an abnormal physical condition of the driver or an abnormal driving state according thereto and warn the driver using information on a physical condition of the driver and driving pattern information of the driver as well as recognizing drowsiness of the driver simply using an image of the face of the driver, thereby assisting safe driving.

In addition, according to the system and method for monitoring a driver of various embodiments of the present disclosure, even when the physical condition of the driver is so bad that the driver cannot drive the vehicle, it is possible to cause the vehicle to safely evacuate to a safe zone through autonomous driving of a relatively basic level using various sensors related to safety of the vehicle provided in the vehicle to aid in traffic accident prevention.

Although the exemplary embodiments of the present disclosure have been disclosed for illustrative purposes, those skilled in the art will appreciate that various modifications, additions and substitutions are possible, without departing from the scope and spirit of the disclosure as disclosed in the accompanying claims.

What is claimed is:

1. A system for monitoring a driver, comprising:
    a first sensor configured to detect first physical condition information of the driver;
    a second sensor configured to detect first driving state information of a vehicle; and
    a controller configured to:
        determine whether a physical condition of the driver is abnormal based on the first physical condition information, and
        determine whether a driving pattern of the driver is abnormal based on comparison result between the first driving state information and big data analysis information obtained by analyzing accumulated driving state information previously detected by the second sensor and stored in a storage, wherein the controller obtains a first driving pattern represented by the first driving state information and compares the first driving pattern and a second driving pattern represented by the big data analysis information.

2. The system according to claim 1, wherein the controller includes the storage configured to store big data analysis values of second physical condition information detected by the first sensor and stored in the storage, and
    wherein the controller is further configured to determine whether a physical condition of the driver is abnormal based on comparison result between the first physical condition information of the driver and the big data analysis values.

3. The system according to claim 2, wherein the controller determines that the driving pattern of the driver is abnormal when a difference between the first driving pattern and the second driving pattern is greater than or equal to a predetermined value, the driving pattern of the driver includes driving habit information of the driver.

4. The system according to claim 1, wherein the first sensor includes a wearable device configured to be worn by the driver, the wearable device configured to:
    detect a heart rate of the driver, and
    transmit the heart rate to the controller through wireless communication.

5. The system according to claim 1, wherein the first sensor includes a heart rate monitor disposed in a steering wheel of the vehicle, the heart rate monitor configured to detect a heart rate of the driver through a hand of the driver in contact with the heart rate monitor.

6. The system according to claim 1,
    wherein the accumulated driving state information previously detected by the second sensor include positions of lanes, change in a yaw value of the vehicle and change in a steering angle indicating a degree of rotation of a steering wheel previously detected by the second sensor.

7. The system according to claim 1, wherein the second sensor includes a camera configured to capture a front view image of the vehicle including the position of lanes, a yaw sensor configured to measure the yaw value of the vehicle, and a steering angle sensor configured to detect the steering angle of the vehicle.

8. The system according to claim 1, wherein the controller is further configured to:
    guide the vehicle to a safe zone, and
    control the vehicle to stop in the safe zone upon determining that at least one of the physical condition of the driver is abnormal or the driving pattern is abnormal.

9. The system according to claim 8, further comprising an image sensor configured to sense objects around the vehicle and capture images around the vehicle,
    wherein the controller determines an outermost lane of a road and an outermost structure of the road on the basis of the images captured by the image sensor, upon determining that at least one of the physical condition of the driver is abnormal or the driving pattern is abnormal, checks following vehicles in a blind-spot through images captured by the image sensor, controls the vehicle to move toward an edge of the road by adjusting a steering wheel of the vehicle while reducing a vehicle speed, and controls the vehicle to stop after arrival at the edge of the road, and wherein the image sensor includes at least one of a camera capturing a front view image of the vehicle, a radar, or a Lidar.

10. The system according to claim 9, wherein the controller further includes a storage including at least one of a deep learning network configured to detect the outermost lane from the images captured by the image sensor or a deep learning network configured to detect the outermost structure of the road, and wherein the controller detects at least one of the outermost lane or the outermost structure by inputting the captured images or an input signal of the image sensor to the deep learning network.

11. A method for monitoring a driver, the method performed a controller, comprising:

receiving first physical condition information of the driver detected by a first sensor of a vehicle and first driving state information of the vehicle detected by a second sensor of the vehicle;

determining whether a physical condition of the driver is abnormal based the first physical condition information;

determining whether a driving pattern of the driver is abnormal based on comparison result between the first driving state information and big data analysis information obtained by analyzing accumulated driving state information previously detected by the second sensor and stored in a storage, the determining whether a driving pattern of the driver is abnormal including;

obtaining a first driving pattern represented by the first driving state information and a second driving pattern represented by the big data analysis information and comparing the first driving pattern and the second driving pattern; and in response to determination that at least one of the physical condition or the driving pattern is abnormal, automatically controlling the vehicle to move to a safe zone.

12. The method according to claim 11, wherein the determining whether the physical condition of the driver is abnormal comprises determining whether the physical condition of the driver is abnormal based on comparison result between the first physical condition information of the driver and the big data analysis values.

13. The method according to claim 12, wherein the driving pattern of the driver is determined abnormal when a difference between the first driving pattern and the second driving pattern is greater than or equal to a predetermined value, wherein the driving pattern of the driver includes driving habit information of the driver.

14. The method according to claim 11, wherein the first sensor includes a wearable device configured to be worn by the driver, the wearable device configured to:

detect a heart rate of the driver, and transmit the heart rate to the controller through wireless communication.

15. The method according to claim 11, wherein the first sensor includes a heart rate monitor disposed in a steering wheel of the vehicle, the heart rate monitor configured to detect a heart rate of the driver through a hand of the driver in contact with the heart rate monitor.

16. The method according to claim 11, wherein the accumulated driving state information previously detected by the second sensor include positions of lanes, change in a yaw value of the vehicle and change in a steering angle indicating a degree of rotation of a steering wheel previously detected by the second sensor.

17. The method according to claim 11, wherein the second sensor includes a camera configured to capture a front view image of the vehicle including the position of lanes, a yaw sensor configured to measure the value of the vehicle, and a steering angle sensor configured to detect the steering angle of the vehicle.

18. The method according to claim 11, further comprising performing autonomous driving control to guide the vehicle to the safe zone and to control the vehicle to stop in the safe zone upon determining that at least one of the physical condition of the driver is abnormal or the driving pattern is abnormal.

19. The method according to claim 18, wherein the performing of the autonomous driving control comprises, upon determining that the physical condition of the driver is abnormal or the driving pattern is abnormal:

detecting an outermost lane or an outermost structure of a road on the basis of objects sensed around the vehicle or images captured around the vehicle by an image sensor;

checking following vehicles through the objects sensed in a blind stop by the image sensor;

controlling the vehicle to move toward an edge of the road by adjusting a steering wheel of the vehicle while reducing a vehicle speed; and controlling the vehicle to stop after arrival at the edge of the road, wherein the image sensor includes at least one of a camera capturing a front view image of the vehicle, a radar, or a Lidar.

20. The method according to claim 19, wherein the performing of the autonomous driving control comprises detecting the outermost lane or the outermost structure by inputting the images to a deep learning network configured to detect the outermost lane from the images or an input signal of the image sensor to a deep learning network configured to detect the outermost structure of the road from the input signal.

* * * * *